(12) United States Patent
Averina et al.

(10) Patent No.: US 10,555,704 B2
(45) Date of Patent: Feb. 11, 2020

(54) SYSTEMS AND METHODS FOR MEDICAL ALERT MANAGEMENT

(71) Applicant: Cardiac Pacemakers, Inc., St. Paul, MN (US)

(72) Inventors: Viktoria A. Averina, Shoreview, MN (US); Pramodsingh Hirasingh Thakur, Woodbury, MN (US); Ramesh Wariar, Blaine, MN (US); Qi An, Blaine, MN (US); Yi Zhang, Plymouth, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 16/025,201

(22) Filed: Jul. 2, 2018

(65) Prior Publication Data

US 2019/0008467 A1    Jan. 10, 2019

Related U.S. Application Data

(60) Provisional application No. 62/528,701, filed on Jul. 5, 2017.

(51) Int. Cl.
   *G08B 1/08*      (2006.01)
   *A61B 5/00*      (2006.01)
   (Continued)

(52) U.S. Cl.
   CPC ............ *A61B 5/746* (2013.01); *A61B 5/4836* (2013.01); *A61B 5/7282* (2013.01); *G08B 21/182* (2013.01); *G16H 50/20* (2018.01)

(58) Field of Classification Search
   CPC ..... A61B 5/746; A61B 5/7275; A61B 5/7282; A61B 5/4836; A61B 5/686; A61B 5/0031;
   (Continued)

(56) References Cited

U.S. PATENT DOCUMENTS

| | | | |
|---|---|---|---|
| 2002/0002325 A1* | 1/2002 | Iliff | G06Q 50/22 600/300 |
| 2009/0054741 A1* | 2/2009 | McAleer | A61B 5/0205 600/301 |

(Continued)

FOREIGN PATENT DOCUMENTS

| | | |
|---|---|---|
| WO | WO-2017172934 A1 | 10/2017 |
| WO | WO-2019010112 A1 | 1/2019 |

OTHER PUBLICATIONS

"International Application Serial No. PCT/US2018/040550, International Search Report dated Sep. 24, 2018", 5 pgs.

(Continued)

*Primary Examiner* — Anh V La
(74) *Attorney, Agent, or Firm* — Schwegman Lundberg & Woessner, P.A.

(57) ABSTRACT

Systems and methods for managing machine-generated alerts of a medical event such as worsening heart failure (WHF) are described. A patient management system includes a patient database of information about a correspondence between a plurality of alert thresholds (ATHs) and corresponding clinical outcome indicators (COIs) for a plurality of patients. A control circuit can query the patient database for a matching patient that meets specific query criteria compared to a target patient, retrieve an ATH-COI correspondence associated with the matching patient, and determine the alert threshold using a user input of a COI and the retrieved ATH-COI correspondence. A medical event detector detects the medical event using physiological signals sensed from the target patient and the determined alert threshold.

20 Claims, 6 Drawing Sheets

(51) Int. Cl.
*G16H 50/20* (2018.01)
*G08B 21/18* (2006.01)

(58) Field of Classification Search
CPC ........ G16H 70/60; G16H 50/70; G16H 50/20;
A61N 1/3702; A61N 1/365; A61N 1/025;
A61N 1/3627; G08B 21/182
USPC .... 340/539.12, 573.1, 539.1, 286.06, 286.07
See application file for complete search history.

(56) References Cited

U.S. PATENT DOCUMENTS

| | | | |
|---|---|---|---|
| 2010/0010585 A1* | 1/2010 | Davis | A61B 5/1116 |
| | | | 607/62 |
| 2013/0116578 A1 | 5/2013 | An et al. | |
| 2013/0267791 A1 | 10/2013 | Halperin et al. | |
| 2016/0022140 A1* | 1/2016 | Colman | A61B 5/746 |
| | | | 340/539.12 |
| 2017/0021184 A1* | 1/2017 | Pavel | A61N 1/3987 |
| 2017/0027474 A1* | 2/2017 | Sharma | A61B 5/0537 |
| 2017/0095160 A1 | 4/2017 | Thakur et al. | |

OTHER PUBLICATIONS

"International Application Serial No. PCT/US2018/040550, Written Opinion dated Sep. 24, 2018", 6 pgs.

\* cited by examiner

SYSTEMS AND METHODS FOR MEDICAL ALERT MANAGEMENT

CLAIM OF PRIORITY

This application claims the benefit of priority under 35 U.S.C. § 119(e) of U.S. Provisional Patent Application Ser. No. 62/528,701, filed on Jul. 5, 2017, which is herein incorporated by reference in its entirety.

TECHNICAL FIELD

This document relates generally to medical systems, and more particularly, to systems, devices and methods for managing alerts for physiological event detection.

BACKGROUND

Implantable medical devices (IMDs) have been used for monitoring patient health condition or disease states and delivering therapies. For example, implantable cardioverter-defibrillators (ICDs) are used to monitor certain abnormal heart rhythms. Some IMDs may be used to monitor progression of a chronic disease, such as worsening of cardiac performance due to congestive heart failure (CHF). In addition to diagnostic capabilities, the IMDs may also provide therapies to treat or alleviate certain medical conditions, such as cardiac electrostimulation therapies to treat cardiac arrhythmias or to rectify cardiac dyssynchrony in CHF patients.

The IMDs may generate alert notification when the occurrence of an alert condition triggers a notification scheme. The alert condition may include a detection of a particular health condition or a medical event, such as a cardiac arrhythmia or worsening heart failure (WHF). The alert notification may be provided to a healthcare provider to signal the patient health condition. Upon being notified, the healthcare provider may review patient medical record or the physiological data stored in the IMD, determine the presence or causes of the medical event, or assess whether a prescribed therapy has resulted in desired therapeutic outcome.

OVERVIEW

Frequent monitoring of CHF patients and timely detection of events indicative of WHF may help reduce healthcare cost associated with HF hospitalization. Identification of patient at an elevated risk of developing WHF may help ensure timely treatment, improve the prognosis and patient outcome, and avoid unnecessary medical interventions and save the overall cost.

Ambulatory medical devices (AMDs) have been used to monitor HF patient, detect events leading to WHF, and alert a healthcare provider about an on-going or future impending WHF event. An alert may be issued before, during, or after the WHF event detection. In some cases, an alert may be issued when a physiological signal or a trend of a physiological signal metric satisfies a particular condition, such as crossing a specified alert threshold. The alert threshold may therefore affect timing of an alert, number of alerts produced, frequency of alerts, or alert durations, among other alert characteristics. Improperly chosen alert threshold may result in undesirable alerts, such as fractured alerts or perpetual alerts. Fractured alerts are multiple separated alerts each having relative short durations. Fracture alerts may be caused by repeated detections and loss of detections of a single underlying WHF event, and are more likely to happen when a patient response to the underlying WHF event fluctuates over time. Perpetual alerts can be manifested as a single sustained alert with a long duration that includes a non-WHF event, or multiple clinically distinguishable WHF events. Neither fracture alerts nor perpetual alerts adequately reflecting the underlying WHF event. When a healthcare provider uses the alert in patient management, the fracture alerts may unnecessarily consume healthcare resources and increase healthcare cost, and the perpetual alerts may not effectively distinguish separate WHF events.

Alert threshold needs to be properly selected to avoid or reduce undesirable alerts such as fracture alerts or perpetual alerts. A carefully programmed, individualized threshold may also accurately detect WHF or identify patient WHF risk with high sensitivity, specificity, or positive predicative value. The alert threshold may be manually selected by a system user such as a clinician, and programmed into a medical even detection and alert system, such as an AMD. In some cases, the medical event detection and alert system may generate a composite signal metric using measurements from multiple physiological sensors, and compare the composite signal metric to the selected alert threshold. The composite signal metric and the threshold may be unitless numbers that does not carry explicit physiological or clinical meaning. This may be challenging for the system user to determine a proper and individualized threshold for a patient. For example, a clinician may find it not readily obvious as to the manner of threshold adjustment, such as direction and/or amount of adjustment, so as to find a proper threshold that may lead to desirable WHF detection and alert performance. The present inventors have recognized a need for technologies that ascribe clinical context to WHF detection thresholds. This may assist clinician or other system users to more efficiently and more effectively program the automated WHF detection and alert system, and therefore to improve HF patient management.

This document discusses, among other things, systems, devices, and methods for managing machine-generated alerts associated with medical events, such as a WHF event. A patient management system may include a medical event detector configured to detect WHF and generate a WHF alert. A patient database may store information about correspondence between a plurality of alert thresholds (ATHs) and corresponding clinical outcome indicators (COIs) for each of a plurality of patients. A control circuit may query the patient database for a matching patient that meets specific query criteria with respect to a target patient, retrieve an ATH-COI correspondence associated with the matching patient, and determine the alert threshold using a user input of a COI and the retrieved ATH-COI correspondence. The medical event detector may detect WHF using one or more physiological signals sensed from the target patient and the determined alert threshold.

Example 1 is a system that comprises a memory circuit, a control circuit, and a medical event detector circuit. The memory circuit may store a patient database including information about a correspondence between a plurality of alert thresholds (ATHs) and corresponding clinical outcome indicators (COIs) for a plurality of patients. The control circuit may query the patient database for at least one matching patient that meets specific query criteria with respect to a target patient, and to retrieve an ATH-COI correspondence associated with the at least one matching patient. The medical event detector circuit may detect a medical event from the target patient using (1) one or more physiological signals and (2) an alert threshold according to the retrieved ATH-COI correspondence, and to generate an alert of the detected medical event.

In Example 2, the subject matter of Example 1 optionally includes the control circuit that may determine the alert threshold using a user input of a COI and the retrieved ATH-COI correspondence. The medical event detector circuit generate the alert of the detected medial event when a measurement of the one or more physiological signals exceeds the determined alert threshold.

In Example 3, the subject matter of any one or more of Examples 1-2 optionally includes the alert threshold that may include a composite signal index threshold, and the medical event detector circuit may generate a composite signal index using a combination of signal metrics derived from the one or more physiological signals, and generate the alert in response to the generated composite signal index exceeding the composite signal index threshold.

In Example 4, the subject matter of any one or more of Examples 1-3 optionally includes the control circuit that may construct and manage the patient database. This may include, for a patient, adjusting the alert threshold to obtain a plurality of ATHs and determine a plurality of COIs corresponding to the plurality of ATHs, and establishing a correspondence between the plurality of ATHs and the plurality of COIs.

In Example 5, the subject matter of any one or more of Examples 1-4 optionally includes the control circuit that may receive information about a symptom or sign of the medical event via an external device communicatively coupled to the control circuit, and determine the plurality of COIs further using the information about the symptom or sign.

In Example 6, the subject matter of any one or more of Examples 1-5 optionally includes the control circuit that may determine a variability of the plurality of COIs for a patient. The established correspondence between the plurality of ATHs and the plurality of COIs may be included in the patient database if the determined variability satisfies a specified condition.

In Example 7, the subject matter of any one or more of Examples 1-6 optionally includes the COI that may include a time to symptom representing a time interval from an onset of the generated alert to a clinical presentation of a symptom or sign of the medical event.

In Example 8, the subject matter of any one or more of Examples 1-7 optionally includes the COI that may include information about a degree of severity of the medical event detected using a corresponding ATH.

In Example 9, the subject matter of Example 8 optionally includes the medical event that may include a worsening heart failure (WHF). The COI may include one or more of: a stable heart failure; a subclinical heart failure requiring no medication change; a non-emergent WHF requiring oral medication change; a non-emergent WHF requiring intravenous therapy; or an emergent WHF.

In Example 10, the subject matter of any one or more of Examples 1-9 optionally includes the COI that may include a detection performance indicator representing statistical accuracy of a detection of the medical event using a corresponding ATH.

In Example 11, the subject matter of any one or more of Examples 1-10 optionally includes the COI that may include an intervention effectiveness indicator representing an efficacy of a therapy delivered in response to a detection of the medical event using a corresponding ATH.

In Example 12, the subject matter of any one or more of Examples 1-11 optionally includes the COI that may include a time to intervention representing a time delay from an onset of the generated alert to delivery of a therapy for treating the medical event.

In Example 13, the subject matter of any one or more of Examples 1-12 optionally include the COI that may include a time to alert resolution representing a time delay from an onset of the generated alert to a reset of the generated alert.

In Example 14, the subject matter of any one or more of Examples 1-13 optionally includes the control circuit that may query the patient database for the at least one matching patient based on patient demographic information.

In Example 15, the subject matter of any one or more of Examples 1-14 optionally includes a therapy circuit that may generate or adjust a therapy in response to the detection of the medical event.

Example 16 is a method that comprises steps of: acquiring a patient database stored in a memory circuit that includes information about correspondence between a plurality of alert thresholds (ATHs) and corresponding clinical outcome indicators (COIs) for a plurality of patients; querying the patient database, via a control circuit, for at least one matching patient that meets specific query criteria with respect to a target patient; retrieving an ATH-COI correspondence associated with the at least one matching patient; and detecting a medical event from the target patient, via a medical event detector circuit, using (1) one or more physiological signals and (2) an alert threshold according to the retrieved ATH-COI correspondence.

In Example 17, the subject matter of Example 16 optionally includes determining the alert threshold using a user input of a COI and the retrieved ATH-COI correspondence, and generate an alert of the detected medical event when a measurement of the one or more physiological signals exceeds the determined alert threshold.

In Example 18, the subject matter of Example 16 optionally includes the alert threshold that may include a composite signal index threshold. The detecting of the medical event includes generating a composite signal index using a combination of signal metrics derived from the one or more physiological signals, and generating the alert in response to the generated composite signal index exceeding the composite signal index threshold.

In Example 19, the subject matter of Example 16 optionally includes, for a patient, adjusting the alert threshold to obtain a plurality of ATHs; determining a plurality of COIs corresponding to the plurality of ATHs, and establishing a correspondence between the plurality of ATHs and the plurality of COIs.

In Example 20, the subject matter of Example 16 optionally include, further comprising: receiving information about a symptom or sign of the medical event via an external device; and determining the plurality of COIs using the information about the symptom or sign.

In Example 21, the subject matter of Example 16 optionally includes the COI that may include one or more of: a time to symptom; a degree of severity of the medical event; a detection performance indicator; an intervention effectiveness indicator; a time to intervention; or a time to alert resolution.

In Example 22, the subject matter of Example 16 optionally includes querying the patient database for the at least one matching patient based on patient demographic information.

The systems, devices, and methods discussed in this document may improve the technology of automated patient alert management. The present document provides a technological solution to a technical challenge of disconnection between detection threshold and the clinical context of WHF detection and alert, identified to exist in conventional HF management systems. In particular, the technology discussed in the present document associates detection parameters such as detection threshold with clinical implications, and establishes an adjustable ATH-COI correspondence. The clinical outcomes represent clinical or physiological consequence or implications of detections under different detection thresholds. A clinician may refer to the ATH-COI correspondence to program a heart failure detection and alert system to detect WHF with fewer undesirable alerts. The present technology discussed herein may help align the medical resources to serve the need of more patients, and save the operational cost in the healthcare facilities. For example, better programming of detection threshold may improve the alert management system's performance in recognizing high-severity WHF events with higher accuracy (i.e., lower false alert rate), yet at little to no additional cost or system complexity. On the other hand, with the reduced number of alerts, fewer unnecessary medical interventions, such as drugs, procedures, or device therapies, may be scheduled, prescribed, or provided to such patients. As a result, overall system cost savings may be realized.

The alert notification evaluation and prioritization discussed in this document may also improve the functionality of a patient management system. In some cases, improved alert management may be achieved without a modification of existing patient AMDs or physiological event detectors. The system memory may be more efficient by storing a smaller number of alerts associated with medical events of higher severity and/or physiological information clinically more relevant to medical diagnosis. With a more efficient alert management, the device battery life can be extended, fewer unnecessary drugs and procedures may be scheduled, prescribed, or provided, and an overall system cost savings may be realized.

Although the discussion in this document focuses alerts of WHF detected by AMDs, this is meant only by way of example and not limitation. It is within the contemplation of the inventors, and within the scope of this document, that the systems, devices, and methods discussed herein may also be used to detect, and alert occurrence of, cardiac arrhythmias, syncope, pulmonary congestion, respiratory disease, or renal dysfunctions, among other medical conditions. Additionally, although systems and methods are described as being operated or exercised by clinicians, the entire discussion herein applies equally to organizations, including hospitals, clinics, and laboratories, and other individuals or interests, such as researchers, scientists, universities, and governmental agencies, seeking access to the patient data.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for managing machine-generated alerts of a medical event. A patient management system includes a patient database of information about correspondence between a plurality of alert thresholds (ATHs) and corresponding clinical outcome indicators (COIs). A control circuit may query the patient database for a matching patient that meets specific query criteria, and to retrieve information about ATH-COI correspondence associated with the matching patient. The system may detect the medical event using one or more physiological signals sensed from the target patient and an alert threshold determined using the retrieved ATH-COI correspondence.

Figure 1:
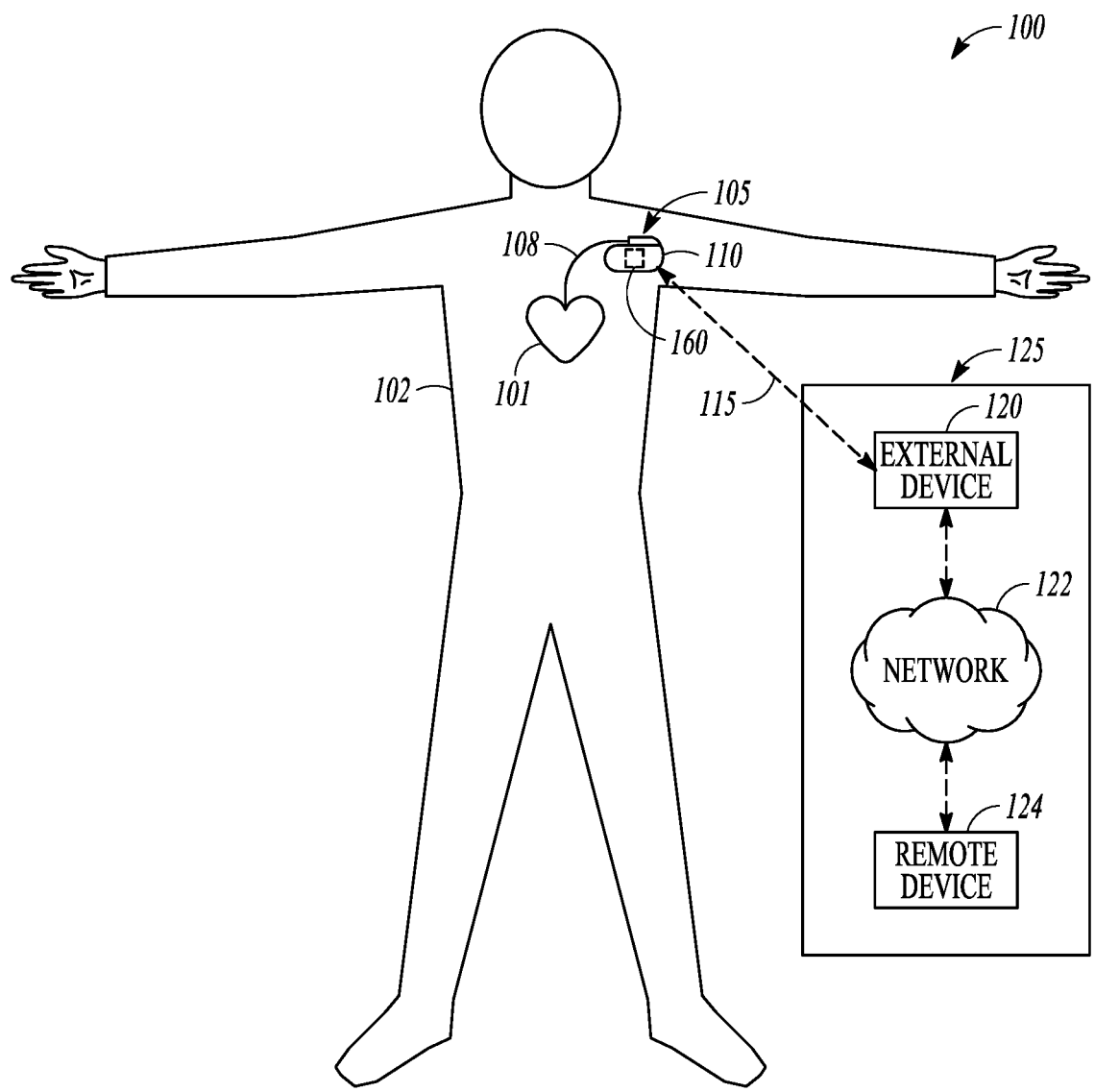
FIG. 1 illustrates generally an example of a patient management system and portions of an environment in which the system may operate.

FIG. 1 illustrates generally an example of a patient management system 100 and portions of an environment in which the system 100 may operate. The patient management system 100 may perform a range of activities, including remote patient monitoring and diagnosis of a disease condition. Such activities can be performed proximal to a patient, such as in the patient's home or office, through a centralized server, such as in a hospital, clinic or physician's office, or through a remote workstation, such as a secure wireless mobile computing device.

The patient management system 100 may include an ambulatory system 105 associated with a patient 102, an external system 125, and a telemetry link 115 providing for communication between the ambulatory system 105 and the external system 125.

The ambulatory system 105 may include an ambulatory medical device (AMD) 110. In an example, the AMD 110 may be an implantable device subcutaneously implanted in a chest, abdomen, or other parts of the patient 102. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The AMD 110 alternatively or additionally may include a subcutaneous medical device such as a subcutaneous monitor or diagnostic device, external monitoring or therapeutic medical devices such as automatic external defibrillators (AEDs) or Holter monitors, or wearable medical devices such as patch-based devices, smart watches, or smart accessories.

By way of example, the AMD 110 may be coupled to a lead system 108. The lead system 108 may include one or more transvenously, subcutaneously, or non-invasively placed leads or catheters. Each lead or catheter may include one or more electrodes. The arrangements and uses of the lead system 108 and the associated electrodes may be determined using the patient need and the capability of the AMD 110. The associated electrodes on the lead system 108 may be positioned at the patient's thorax or abdomen to sense a physiological signal indicative of cardiac activity, or physiological responses to diagnostic or therapeutic stimulations to a target tissue. By way of example and not limitation, and as illustrated in FIG. 1, the lead system 108 may be surgically inserted into, or positioned on the surface of, a heart 101. The electrodes on the lead system 108 may be positioned on a portion of a heart 101, such as a right atrium (RA), a right ventricle (RV), a left atrium (LA), or a left ventricle (LV), or any tissue between or near the heart portions. In some examples, the lead system 108 and the associated electrodes may alternatively be positioned on other parts of the body to sense a physiological signal containing information about patient heart rate or pulse rate. In an example, the ambulatory system 105 may include one or more leadless sensors not being tethered to the AMD 110 via the lead system 108. The leadless ambulatory sensors may be configured to sense a physiological signal and wirelessly communicate with the AMD 110.

The AMD 110 may be configured as a monitoring and diagnostic device. The AMD 110 may include a hermetically sealed can that houses one or more of a sensing circuit, a control circuit, a communication circuit, and a battery, among other components. The sensing circuit may sense a physiological signal, such as by using a physiological sensor or the electrodes associated with the lead system 108. Examples of the physiological signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, right ventricular (RV) pressure, left ventricular (LV) coronary pressure, coronary blood temperature, blood oxygen saturation, one or more heart sounds, intracardiac acceleration, physical activity or exertion level, physiological response to activity, posture, respiration rate, tidal volume, respiratory sounds, body weight, or body temperature.

In an example, the AMD 110 may include a detector circuit 160 for detecting a medical event from the sensed physiological signals. Examples of the medical event include cardiac arrhythmias, worsening of a chronic medical condition, such as worsening heart failure (WHF). In another example, the medical event may include patient-triggered events. The detector circuit 160 may query a patient database for a matching patient that meets specific query criteria. The databased may contain information about correspondence between a plurality of alert thresholds (ATHs) and corresponding clinical outcome indicators (COIs) for a plurality of patients. The detector 160 may retrieve information about ATH-COI correspondence associated with the matching patient, and detect WHF using one or more physiological signals and an alert threshold taken from the retrieved information about ATH-COI correspondence.

The AMD 110 may alternatively be configured as a therapeutic device configured to treat arrhythmia or other heart conditions. The AMD 110 may additionally include a therapy unit that may generate and deliver one or more therapies. The therapy may be delivered to the patient 102 via the lead system 108 and the associated electrodes. The therapies may include electrical, magnetic, or other types of therapy. The therapy may include anti-arrhythmic therapy to treat an arrhythmia or to treat or control one or more complications from arrhythmias, such as syncope, congestive heart failure, or stroke, among others. Examples of the anti-arrhythmic therapy may include pacing, cardioversion, defibrillation, neuromodulation, drug therapies, or biological therapies, among other types of therapies. In an example, the therapies may include cardiac resynchronization therapy (CRT) for rectifying dyssynchrony and improving cardiac function in CHF patients. In some examples, the AMD 110 may include a drug delivery system such as a drug infusion pump to deliver drugs to the patient for managing arrhythmias or complications from arrhythmias.

The external system 125 may include a dedicated hardware/software system such as a programmer, a remote server-based patient management system, or alternatively a system defined predominantly by software running on a standard personal computer. The external system 125 may manage the patient 102 through the AMD 110 connected to the external system 125 via a communication link 115. This may include, for example, programming the AMD 110 to perform one or more of acquiring physiological data, performing at least one self-diagnostic test (such as for a device operational status), analyzing the physiological data to detect a cardiac arrhythmias, or optionally delivering or adjusting a therapy to the patient 102. Additionally, the external system 125 may receive device data from the AMD 110 via the communication link 115. Examples of the device data received by the external system 125 may include real-time or stored physiological data from the patient 102, diagnostic data such as detection of cardiac arrhythmias or events of worsening heart failure, responses to therapies delivered to the patient 102, or device operational status of the AMD 110 (e.g., battery status and lead impedance). The telemetry link 115 may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible.

By way of example and not limitation, the external system 125 may include an external device 120 in proximity of the AMD 110, and a remote device 124 in a location relatively distant from the AMD 110 in communication with the external device 120 via a telecommunication network 122. Examples of the external device 120 may include a programmer device.

The remote device 124 may be configured to evaluate collected patient data and provide alert notifications, among other possible functions. In an example, the remote device 124 may include a centralized server acting as a central hub for collected patient data storage and analysis. The server may be configured as a uni-, multi- or distributed computing and processing system. The remote device 124 may receive patient data from multiple patients including, for example, the patient 102. The patient data may be collected by the AMD 110, among other data acquisition sensors or devices associated with the patient 102. The server may include a memory device to store the patient data in a patient database. The server may include an alert analyzer circuit to evaluate the collected patient data to determine if specific alert condition is satisfied. Satisfaction of the alert condition may trigger a generation of alert notifications. In some examples, the alert conditions alternatively or additionally may be evaluated by the AMD 110. By way of example, alert notifications may include a Web page update, phone or pager call, E-mail, SMS, text or "Instant" message, as well as a message to the patient and a simultaneous direct notification to emergency services and to the clinician. Other alert notifications are possible.

The remote device 124 may additionally include one or more locally configured clients or remote clients securely connected over the network 122 to the server. Examples of the clients may include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning.

The network 122 may provide wired or wireless interconnectivity. In an example, the network 122 may be based on the Transmission Control Protocol/Internet Protocol (TCP/IP) network communication specification, although other types or combinations of networking implementations are possible. Similarly, other network topologies and arrangements are possible.

One or more of the external device 120 or the remote device 124 may output the detected medical events to a system user such as the patient or a clinician, or to a process including, for example, an instance of a computer program executable in a microprocessor. In an example, the process may include an automated generation of recommendations for anti-arrhythmic therapy, or a recommendation for further diagnostic test or treatment. In an example, the external device 120 or the remote device 124 may include a respective display unit for displaying the physiological or functional signals, or alerts, alarms, emergency calls, or other forms of warnings to signal the detection of arrhythmias. In some examples, the external system 125 may include an external data processor configured to analyze the physiological or functional signals received by the AMD 110, and to confirm or reject the detection of arrhythmias. Computationally intensive algorithms, such as machine-learning algorithms, may be implemented in the external data processor to process the data retrospectively to detect cardia arrhythmias.

Portions of the AMD 110 or the external system 125 may be implemented using hardware, software, firmware, or combinations thereof. Portions of the AMD 110 or the external system 125 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
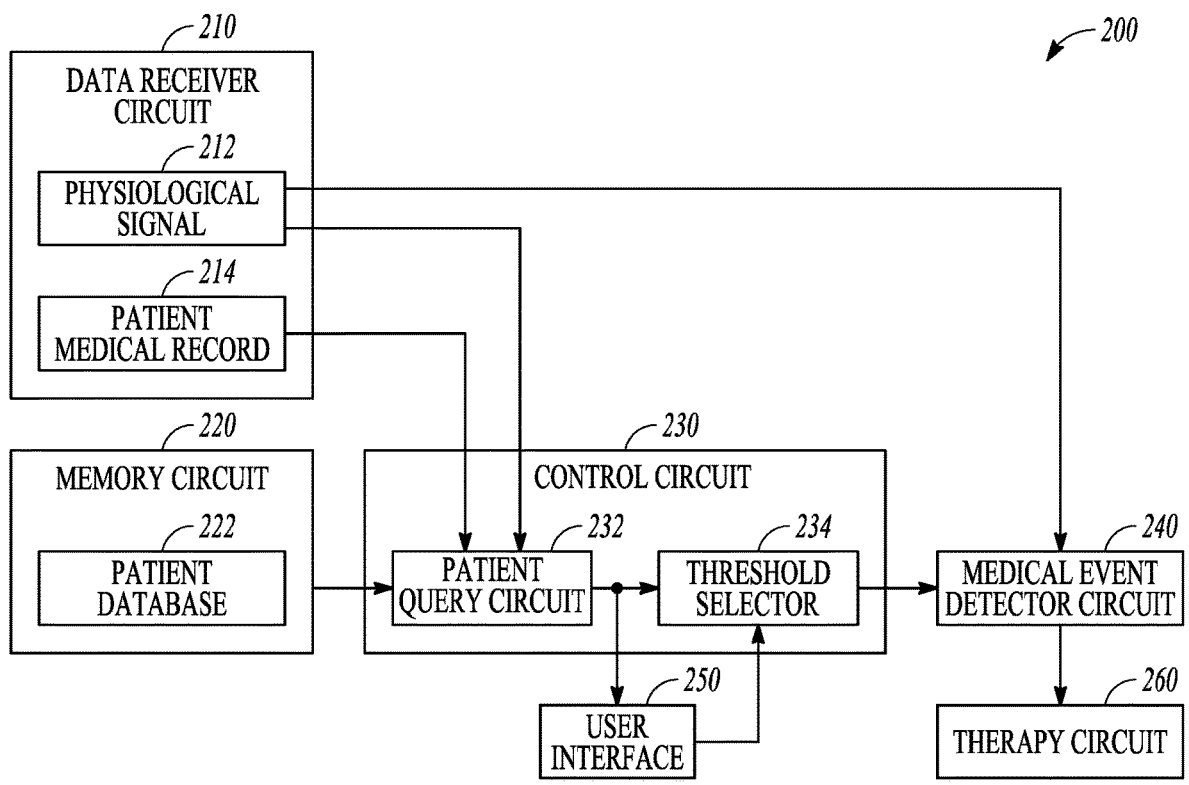
FIG. 2 illustrates generally an example of a medical event detection system configured to detect a medical event such as worsening heart failure (WHF).

FIG. 2 illustrates generally an example of a medical event detection system 200 that may be configured to detect WHF. The medical event detection system 200 may include one or more of a data receiver circuit 210, a memory circuit 220, a control circuit 230, a medical event detector circuit 240, and a user interface 250. The medical event detection system 200 may additionally be configured as a therapeutic system that includes a therapy circuit 260 for delivering a therapy to treat a disease or to alleviate a medical condition.

At least a portion of the medical event detection system 200 may be implemented in the AMD 110, the external system 125 such as one or more of the external device 120 or the remote device 124, or distributed between the AMD 110 and the external system 125. In an example, the data receiver circuit 210, the medical event detector circuit 240, and the optional therapy circuit 260 may be implemented in an AMD. The memory circuit 220, the control circuit 230 and the user interface 250 may be implemented in the external system 125, such as in a programmer or a remote patient management system. The external system 125 may determine desired WHF detection parameter values, such as a detection threshold, and program the AMD 110 with the desired parameter values via the communication link 115. The AMD 110 may detect future events leading to WHF using the desired WHF detection parameter value, or operationally deliver a HF therapy in response to the WHF detection.

The data receiver circuit 210 may receive one or more physiological signals 212 sensed from a patient. In an example, the data receiver circuit 210 may be coupled to a sensor circuit that includes a sense amplifier circuit to sense one or more physiological signals from a patient via one or more implantable, wearable, or otherwise ambulatory sensors or electrodes associated with the patient. The sensors may be incorporated into, or otherwise associated with an ambulatory device such as the AMD 110. Examples of the physiological signals may include surface electrocardiography (ECG) sensed from electrodes placed on the body surface, subcutaneous ECG sensed from electrodes placed under the skin, intracardiac electrogram (EGM) sensed from the one or more electrodes on the lead system 108, thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal such as sensed by an ambulatory accelerometer or acoustic sensors, physiological response to activity, apnea hypopnea index, one or more respiration signals such as a respiration rate signal or a tidal volume signal, brain natriuretic peptide (BNP), blood panel, sodium and potassium levels, glucose level and other biomarkers and bio-chemical markers, among others. The sensor circuit may include one or more sub-circuits to digitize, filter, or perform other signal conditioning operations on the received physiological signal.

In some examples, the physiological signals 212 may be stored in a data storage device, such as an electronic medical record (EMR) system. The data receiver circuit 210 may receive a physiological signal from the data storage device in response to a data retrieval command from a system user. The data receiver circuit 210 may also receive patient medical record 214 from a system user, or retrieve the information from the EMR system. Examples of the patient medical record 214 may include patient demographic information, such as age, race, gender, cigarette smoking, hypertension, diabetes, or obesity, among others. The patient medical record 214 may include patient medical history and treatment received, or other contextual information such as time of day, circumstance or daily life contexts, patient environment, economic situation, medical care facilities, or caretaker responsibilities. The patient medical record 214 may be used by the control circuit 230 to identify a matching patient from a patient database, as to be discussed in the following.

The memory circuit 220 may be configured to store parameters used for detecting a target medical event such as WHF. Intermediate calculations and WHF detection information may be stored in the memory circuit 220. The memory circuit 220 may store a patient database 222, which includes, for each of a plurality of patients, information about correspondence between a plurality of alert thresholds (ATHs) and corresponding clinical outcome indicators (COIs). The ATHs may be used for detecting the target medical event such as WHF. For example, the medical event detector circuit 240 may trend a physiological signal over time, and compare the trended signal metric to the ATH to detect WHF.

The ATH may include an onset threshold (TO). An onset of the target medical event is detected if the signal metric trend exceeds the TO. Additionally or alternatively, the ATH may include a reset threshold (TR). A termination of the detected target medical event is detected if the signal metric falls below the TR. The thresholds TO and TR may have substantially identical values. Alternatively, the onset threshold TO may be greater than the reset threshold. In some examples, only values for the onset threshold TO are included in the ATH-COI correspondence. The reset threshold TR may be empirically determined as a function of the onset threshold TO. For example, the TR may be linearly related to TO, that is, TR=w·TO. The weight factor w may be between zero and one such that TR is less than TO.

Different alert threshold ATHs value may correspond to different clinical outcome COIs. As previously discussed, ATH may be a unitless number that does not carry explicit physiological or clinical meaning. In contrast, the COIs may provide a clinical context that WHF detection and ATH operate on. In various examples, COI may indicate a time to symptom, a time to intervention, information about presence, severity, or type of the WHF, or a statistical performance of the WHF detector at different ATH values. The database of the ATH-COI correspondence stored in the memory circuit 220 therefore establishes an association between the detection parameter such as alert threshold and the clinical outcome. Such an association may assist a clinician to program WHF detection and alert more effectively by selecting the ATH that corresponds to a desired clinical outcome.

In addition to the ATH-COI correspondence, the patient database 222 may include medical record information of the plurality of patients included in the database. Similar to the patient medical record 214 received from the target patient, the patient medical record information in the patient database 222 may include patient demographics, medical and treatment history, among others. The patient database 222 may additionally include information of the type of physiological signals, or signal metrics derived from the physiological signals, that are used for comparing to the ATH and for establishing the ATH-COI correspondence. The patients in the patient database 222 may be indexed by their medical record information, or the type of physiological signals or signal metrics information. The patient database 222 may be searchable by the medical record information or the physiological signal or signal metrics used for detecting the target event. Examples of the ATH-COI correspondence, and the establishment and maintenance of the database of the ATH-COI correspondence, are discussed below such as with reference to FIG. 3.

The control circuit 230 may include one or more sub-circuits to manage the medical data associated with the received events. Alternatively, the control circuit 230 may be implemented as a part of a microprocessor circuit that may execute a set of instructions of performing the functions, methods, or techniques described herein. By way of example and not limitation, the sub-circuits may include one or more of a patient query circuit 232 or a threshold selector 234. The patient query circuit 232 may query the patient database 222 for one or more matching patients that meet specific query criteria with respect to a target patient. As illustrated in FIG. 2, the patient query circuit 232 may be coupled to the data receiver circuit 210 to receive one or more of the patient medical record 214, or the physiological signal 212. In an example, the patient query circuit 232 may query the patient database 222 using one or more patient medical record, such as patient demographic information, of the target patient. The patient query circuit 232 may find a matching patient from the patient database 222 who has substantially the same demographic information, medical history, or treatment history as the target patient, such as patient age within a specified range, heart failure events occurred within a specified period, or type of intervention treatments received within a specified period. In another example, the patient query circuit 232 may query the patient database 222 using the physiological signal received at 210 or signal metrics of the target patient. The patient query circuit 232 may find a matching patient from the patient database 222 whose ATH-COI is established using substantially the same physiological signals or signal metrics as those received for the target patient. In some examples, the patient query circuit 232 may query the patient database 222 using both the patient medical record and the physiological signal or signal metrics of the target patient, optionally together with other query objects such as patient contextual information. In some examples, the query objects, such as the patient medical record, the physiological signal or signal metrics, or contextual information, may be specified, selected, or adjusted by a user, such as a clinician, via the user interface 250. In other examples, if a specific match is not found in the patient database 222 for a set of query criteria, a closest match may be provided, such as the specific query results with a computed matching score, to a user, such as a clinician, for confirmation. In other examples, the closest matching patient is found and a confidence score between the target patient and the matching patient is provided.

If at least one matching patient is found from the patient database 222, the patient query circuit 232 may retrieve the information about ATH-COI correspondence associated with the matching patient. The retrieved ATH-COI may be output to a user (e.g., a clinician) such as displayed on a display of the user interface 250. The user may identify a desired COI from the retrieved information about the ATH-COI correspondence. In an example, the COI indicates a time to symptom appearance (TSA), which may be measured from the time instant when the physiological signal or the signal metric trend exceeds the selected ATH to the time instant when the patient demonstrates a WHF symptom or a WHF sign. The user may specify a desired TSA value. The threshold selector 234 may select an alert threshold that corresponds to the specified TSA value, according to the ATH-COI correspondence. In another example, the COI may include a WHF type or WHF severity, and the threshold selector 234 may select an alert threshold that corresponds to a user specified WHF type or WHF severity.

The user interface 250 may include an input unit and an output unit. In an example, at least a portion of the user interface 250 may be implemented in the external system 125. The input unit may receive user input for identifying a desired COI from the ATH-COI correspondence of a matching patient, or for programming the medical event detector circuit 240 or the optional therapy circuit 260. The input unit may include an input device such as a keyboard, on-screen keyboard, mouse, trackball, touchpad, touch-screen, or other pointing or navigating devices. The output unit may include circuitry configured to schedule a human-perceptible notification of the detected WHF event. The output unit may include a display for displaying the patient physiological signal 212, the patient medical record 214, the information about ATH-COI correspondence associated with the matching patient, information about the detected WHF event, and other intermediate measurements or computations. The output unit may include a printer for printing hard copies of the detection information. The information may be presented in a table, a chart, a diagram, or any other types of textual, tabular, or graphical presentation formats. The presentation of the output information may include audio or other media format. In an example, the output unit may generate alerts, alarms, emergency calls, or other forms of warnings to signal the system user about the detected WHF event.

The medical event detector circuit 240 may detect from the physiological signal 212 a medical event, such as an event indicative of worsening heart failure (WHF), and generate an alert corresponding to the detected medical event. The medical event detector circuit 240 may generate a signal metric from a physiological signal 212. The trend of the signal metric may be compared to the selected threshold provided by the threshold selector 234 to determine an onset or a termination of the medical event. In some examples, the medical event detector circuit 240 may generate a composite signal index using a combination of signal metrics derived from the one or more physiological signals. Examples of the signal metrics may include heart rate, heart rate variability, respiratory rate, rapid-shallow breathing index, one or more heart sounds components such as first (S1), second (S2), third (S3), or fourth (S4) heart sound, a ratio of one HS component to another HS component, thoracic impedance, physical activity or exertion level, among others. The medical event detector circuit 240 may trend the composite signal index over time, and detect WHF and generate a WHF alert when the composite signal index exceeds the selected threshold. In an example, the selected threshold includes an onset threshold TO, and the medical event detector circuit 240 may detect WHF onset using the onset threshold TO. The selected threshold may additionally include a reset threshold TR, and the medical event detector circuit 240 may additionally detect WHF termination using the reset threshold TR. The WHF alert may begin at the detected WHF onset and sustain at least up to the detected WHF termination.

In some examples, the medical event detector circuit 240 may process the signal metric trend and generate a predictor trend indicating temporal changes of the signal metric trend. The temporal change may be calculated as a difference between short-term values and baseline values. In an example, the short-term values may include statistical values such as a central tendency of the measurements of the signal metric within a short-term window of a first plurality of days. The baseline values may include statistical values such as a central tendency of the measurements of the signal metric within a long-term window of a second plurality of days preceding the short-term window in time. In some examples, the predictor trend may be determined using a linear or nonlinear combination of the relative differences between multiple short-term values corresponding to multiple first time windows and multiple baseline values corresponding to multiple second time windows, wherein the differences may be scaled by respective weight factors which may be based on timing information associated with corresponding multiple short-term window, such as described by Thakur et al., in U.S. Patent Application No. 62/236,416, entitled "PREDICTIONS OF WORSENING HEART FAILURE", which is herein incorporated by reference in its entirety.

The optional therapy circuit 260 may be configured to deliver a therapy to the patient in response to the detection of WHF event. Examples of the therapy may include electrostimulation therapy delivered to the heart, a nerve tissue, other target tissues, a cardioversion therapy, a defibrillation therapy, or drug therapy including delivering drug to a tissue or organ. In some examples, the therapy circuit 260 may modify an existing therapy, such as adjust a stimulation parameter or drug dosage.

Systems, devices, and methods discussed in this document may also be suitable for detecting various sorts of chronic diseases including, for example, heart failure, coronary artery disease, chronic obstructive pulmonary disease, or chronic kidney disease, among many others. For example, an ATH-COI correspondence may be established and used to detect one or more physiological events with less undesirable alerts.

Figure 3:
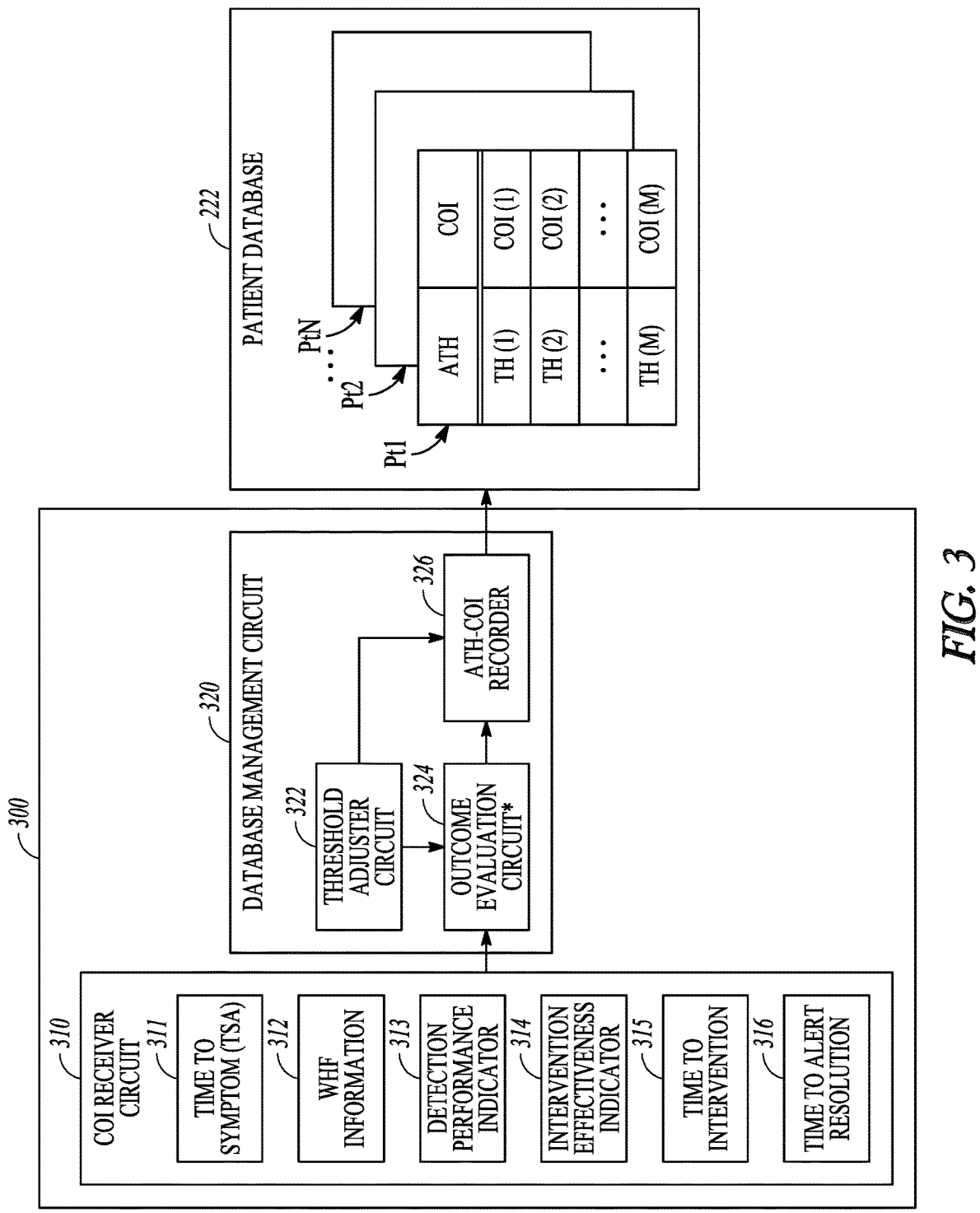
FIG. 3 illustrates generally an example of a system for establishing and maintaining a patient database of correspondence between medical alert thresholds (ATHs) and clinical outcome indicators (COIs) for one or more patients.

FIG. 3 illustrates generally an example of a system 300 for establishing and maintaining a patient database 222 of correspondence between medical alert thresholds (ATHs) and clinical outcome indicators (COIs) for one or more patients. The system 300 may be implemented in the external system 125. The searchable patient database 222 created and maintained by the system 300 may be used by the medical event detection system 200 to identify desired detection parameter, such as a desired detection threshold for detecting WHF event.

The system 300 may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general-purpose processor that may receive and execute a set of instructions of performing the functions, methods, or techniques described herein.

The system 300 may include circuit sets comprising one or more other circuits or sub-circuits, such as a COI receiver circuit 310 and a database management circuit 320. These circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The COI receiver circuit 310 may be configured to receive one or more clinical outcome indicators indicating patient response to the detection of WHF under different detection parameters such as detection thresholds, or detector performance and its clinical implications when the detector is configured to detect WHF using different detection parameters. In an example, the COI receiver circuit 310 may be a part of the user interface 250, and configured to receive user input of one or more COIs. In another example, the COI receiver circuit 310 may be included in a mobile device, such as a smart phone, a tablet, or other wearable or handheld device. The mobile device may be configured to execute an application software ("mobile app") for receiving, processing, or transmitting user input of COIs. The mobile device may have a user interface configured to receive patient input of one or more COIs. Various information may be displayed on the user interface to motivate the user to enter the COIs. In an example, a dashboard with aggregate statistics of COIs under different thresholds may be displayed. In another example, the user's pattern of usage of the application and frequency of database update may be compared to those of other users, and a relative standing or other statistics from that comparison may be presented to the user. In yet another example, the ATH-COI correspondence of the matching patients, or the statistics computed therefrom, may be provided to the user to motivate user participation of COI input and patient database update. Additionally, if some COIs are difficult to obtain directly from the patient, other individuals such as a healthcare professional may help provide COI information. Other sources such as patient electronic medical record system may also be referenced to obtain the desired COI information.

By way of example and not limitation, the received COIs may include one or more of a time to symptom (TSA) 311, WHF information 312, a detection performance indicator 313, an intervention effectiveness indicator 314, a time to intervention 315, and a time to alert resolution 316. The TSA 311 may be measured from an alert onset to a clinical presentation of WHF symptom or sign. TSA thus represents an early warning window before WHF becomes symptomatic. The TSA may be related to the detection threshold selection. For example, a WHF detector operated under a higher detection threshold may be less sensitive to a WHF event. This may lead to a delayed alert of WHF onset detection, and thus a shorter early warning window, or a shorter TSA. If a longer pre-symptom warning window is desired (e.g., for arrangement of clinic visit or preventive therapies or patient interventions), then a longer TSA may be desired.

The WHF information 312 may indicate presence or absence, or a degree of severity, of WHF when the alert is provided at the time corresponding to the WHF detection thresholds. Because detection parameters such as detection threshold may affect the time of alert onset during the course of HF progression, the detection threshold is related to WHF severity at different phases of WHF progression. The severity may be assessed by a clinician, such as during an office visit, via telephone calls or remote patient monitoring. The WHF information may include categorical descriptors such as a stable heart failure, a subclinical heart failure requiring no medication change, a non-emergent WHF requiring oral medication change, a non-emergent WHF requiring intravenous therapy, or an emergent WHF. The WHF information may alternatively be represented by numerical values such as in a scale of one to ten, where a larger number indicates a higher severity. The numerical value may also be assigned to different categories of the WHF assessment as discussed above. In some examples, the WHF information 312 may include type of the WHF events, such as WHF due to congestion, or WHF due to low perfusion, among others.

The detection performance indicator 313 may represent a statistical performance of a WHF detection algorithm operated under certain detection thresholds. Examples of the statistical performance may include sensitivity, specificity, positive predictive value (PPV), negative predicative value (NPV), false positive detection rate, or false negative detection rate, among others. The statistical performance and its relation to detection threshold may be represented by a receiver operating characteristic (ROC) curve, which graphically depicts detection sensitivity against false positive rate at different operating points of the detection thresholds. A desired detection performance (e.g., desired sensitivity and false positive detection rate) thus corresponds to a desired detection threshold. For example, a lower detection threshold (such as the onset threshold TO) may correspond to a higher sensitivity to WHF, along with a higher false positive detection rate and a lower PPV. In some cases, the detection performance indicator 313 such as PPV may be related to not only the detection threshold, but also the duration of the early warning window, or the TSA as previously discussed. For example, a longer TSA may lead to a higher PPV.

The intervention effectiveness indicator 314 may represent an efficacy of a heart failure therapy delivered in response to a WHF alert corresponding to certain detection threshold. The intervention may include administration of medication, initiation or adjustment of a therapy, hospitalization, among others. The effectiveness of intervention may be assessed by a clinician. The effectiveness of an intervention is related to the time of alert onset during the course of HF progression. A lower detection threshold (such as the onset threshold TO) may lead to an early WHF detection and an early WHF alert, and thus an early intervention before the WHF becomes symptomatic or deteriorates to decompensation, which may yield better prognosis in some HF patients.

The time to intervention 315 may represent a time delay from an onset of the generated alert to delivery of a heart failure therapy. The time to intervention 315 may be related to the detection threshold selection. For example, a WHF detector operated on a higher detection threshold may be less sensitive to a WHF event, which may lead to a delayed alert of the WHF onset detection. This may result in a shorter pre-therapy warning time before the initiation or adjustment of a heart failure therapy. If a longer pre-therapy warning window is desired, then a longer time to intervention may be desired.

The time to alert resolution 316 is duration of alert, from alert onset to alert termination. Alert termination occurs when the physiological signal or the signal metric falls below the reset threshold TR. The TSA 311, the time to intervention 315, and the time to alert resolution 316 may all be measured from the alert onset time (which may depend on the onset threshold TO), but they are related to different clinical events. In an example, the WHF symptom or sign may appear before any HF intervention, and the alert may sustain until, or beyond, the initiation of HF intervention. In some examples, other COIs representing temporal relationship among the various clinical events may be received by the COI receiver circuit 310, such as a time interval from symptom appearance to HF intervention, a time interval from symptom appearance to alert termination, or a time interval from HF intervention to alert termination, among others.

The database management circuit 320 may be configured to construct and manage a patient database of ATH-COI correspondence for a plurality of patients. The database management circuit 320 may include a threshold adjuster circuit 322, an outcome evaluation circuit 324, and an ATH-COI recorder 326. The threshold adjuster circuit 322 may adjust the detection thresholds, and the outcome evaluation circuit 324 may evaluate one or more of the COIs 311-316 under different detection thresholds. By way of example and not limitation, the database management circuit 320 may receive information about the clinical presentation of WHF symptom or sign. The threshold adjuster circuit 322 may set a first alert threshold to detect WHF. The outcome evaluation circuit 324 may compute a first TSA corresponding to the first threshold. The threshold adjuster circuit 322 may then adjust the threshold to a different second alert threshold to detect WHF. The outcome evaluation circuit 324 may compute a second TSA corresponding to the second threshold. In an example, the threshold adjuster circuit 322 may automatically adjust the detection threshold according to a testing protocol. The test protocol may include a plurality of specified thresholds, or a scheme for incrementing or decrementing the threshold value between specified lower and upper bounds at specified step size. The outcome evaluation circuit 324 may measure the TSA at each threshold value. Other COIs, such as any of the COIs 311-316, may be similarly evaluated at different thresholds.

The ATH-COI recorder 326, coupled to the threshold adjuster circuit 322 and the outcome evaluation circuit 324, may establish or update a patient database 222 by writing the correspondence between the alert thresholds and the corresponding COI measurements into a memory circuit 220. As illustrated in FIG. 3, the ATH-COI correspondence may be constructed and maintained for each patient. The ATH-COI correspondence may be implemented as a table, an associative array, or other types of data structure in the patient database 222.

The patient database 222 may be indexed by one or more patient identifiers, such that the patient database 222 is searchable using one or more patient identifiers as query objects. In an example, the patients in the patient database 222 may be indexed by their medical record information, such as one or more of patient demographic information, medical history, or treatment history, among others. The patient query circuit 232 may query the patient database 222 using one or more patient medical record of the target patient, and search for a matching patient in the patient database 222 who has substantially the same queried medical record as the target patient. In another example, the patients in the patient database 222 may be indexed by the type of physiological signals or signal metrics information (such as impedance trend, S3 heart sound trend, or a composite signal metrics trend generated using heart rate, impedance, and S3 trend). The patient query circuit 232 may query the patient database 222 using the physiological signal received at 210 or signal metrics of the target patient, and search for a matching patient in the patient database 222 who has substantially the same physiological signals or signal metrics as those received for the target patient. In some examples, the patient query circuit 232 may query the patient database 222 using both the patient medical record and the physiological signal or signal metrics of the target patient, optionally together with other query objects such as patient contextual information. In some examples, the query objects, such as the patient medical record, the physiological signal or signal metrics, or contextual information, may be specified, selected, or adjusted by a user such as a clinician, via the user interface 250. Through the query, the patient query circuit 232 may search for a matching patient and determine the detection threshold for the target patient in detecting future events of WHF.

The database management circuit 320 may update the patient database 222 periodically, or in response to a trigger event or user command. In an example, the database management circuit 320 may integrate new patients and their corresponding ATH-COI correspondences into the patient database 222. In some examples, the database management circuit 320 may merge two or more ATH-COI correspondences of two or more patients who have similar medical record information (e.g., patients Pt1 and Pt2 who have similar demographics) or other specified patient characteristics into an aggregated ATH-COI correspondence. This may improve the memory usage and the efficiency of patient query.

Figure 4:
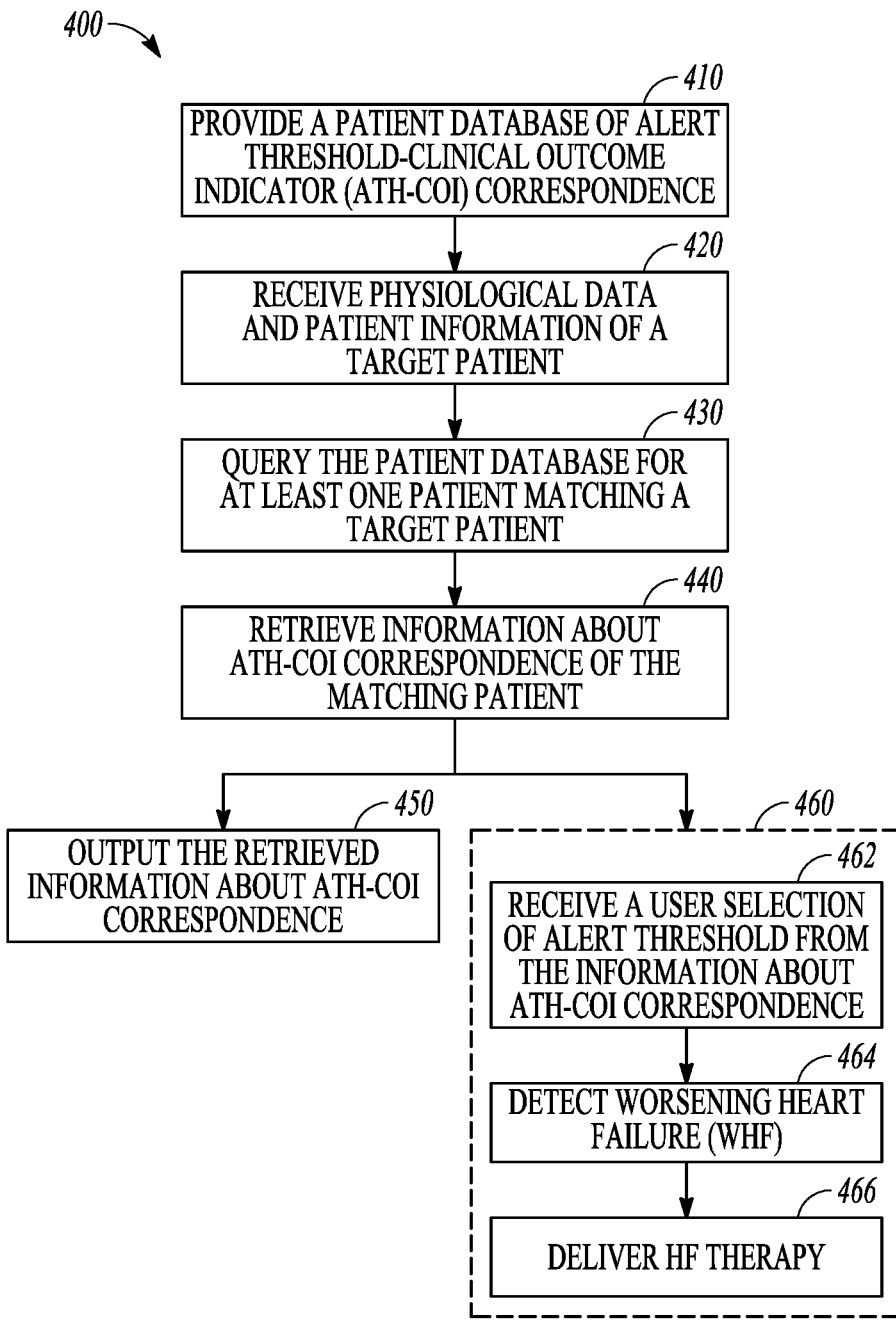
FIG. 4 illustrates generally an example of a method for managing device-generate alert of a medical event.

FIG. 4 illustrates generally an example of a method 400 for managing device-generate alert of a target medical event such as worsening heart failure (WHF). The method 400 may be implemented and executed in an ambulatory medical device such as an implantable or wearable medical device, or in a remote patient management system. In an example, the method 400 may be implemented in, and executed by, the AMD 110, one or more devices in the external system 125, or the alert management systems 200 or 400.

The method 400 begins at 410, where a patient database of correspondence between alert thresholds (ATHs) and clinical outcome indicators (COIs) is provided for use in a process of identifying desired detection parameter, such as a desired threshold value for detecting WHF event. The ATH may include an onset threshold for detecting an onset of WHF event, or a reset threshold to detect termination of a detected WHF event. Programming an individualized detection threshold ATH for a particular patient to achieve desirable WHF detection performance may be challenging in certain cases, at least because the ATH may not carry explicit physiological or clinical meaning. In contrast, the COIs may provide a clinical context that WHF detection and ATH operate on, and different ATH value may correspond to different clinical outcome. The ATH-COI correspondence discussed in this document establishes a connection between the detection parameter such as the ATH and the clinical outcome of HF management, which may help clinician identify the ATH corresponding to a desired clinical outcome.

The COIs include measurements or indicators of patient response to the detection of WHF, or detector performance and its clinical implications when the detector is tuned to detect WHF using different detection thresholds. Examples of the COIs may include one or more of a time to symptom (TSA) 311, WHF information 312, a detection performance indicator 313, an intervention effectiveness indicator 314, a time to intervention 315, and a time to alert resolution 316, as previously discussed with reference to FIG. 3.

In addition to the ATH-COI correspondence for each of a plurality of patients, the patient database 222 may include medical record information of the plurality of patients included in the database. The patient database 222 may additionally include information of the type of physiological signals, or signal metrics derived from the physiological signals, that are used for comparing to the ATH and for establishing the ATH-COI correspondence. The patients in the patient database 222 may be indexed by their medical record information, or the type of physiological signals or signal metrics information. The patient database may be created using the system 300 as discussed previously with reference to FIG. 3. Examples of methods for constructing the maintaining the patient database of the ATH-COI correspondence are discussed below, such as with reference to FIG. 5.

At 420, physiological data and patient information such as medical record of a target patient may be received. The medical data may include one or more physiological signals such as received by the data receiver circuit 210. Examples of the physiological signals may include a cardiac electrical signal, such as an electrocardiography (ECG) or an intracardiac electrogram (EGM), thoracic or cardiac impedance signal, arterial pressure signal, pulmonary artery pressure signal, left atrial pressure signal, RV pressure signal, LV coronary pressure signal, heart sounds or endocardial acceleration signal, physiological response to activity, apnea hypopnea index, one or more respiration signals such as a respiration rate signal or a tidal volume signal, among others. The sensed physiological signal may be pre-processed, including one or more of signal amplification, digitization, filtering, or other signal conditioning operations. In some examples, signal metrics such as timing parameters, or statistical or morphological parameters may be detected from the sensed physiological signal. In some examples, contextual data such as time of day, temperature, environmental parameters, or patient medical record information may additionally be received at 410. Examples of the patient medical record 214 include patient demographic information, such as age, race, gender, cigarette smoking, hypertension, diabetes, or obesity, among others; patient medical history and treatment received; or other contextual information such as circumstance or daily life contexts, economic situation, medical care facilities, or caretaker responsibilities. In some examples, the physiological signals or the patient medical record may be stored in a storage device, such as an electronic medical record (EMR) system.

At 430, the patient database may searched for any patient in the patient base that matches the target patient according to some specified criteria, such as by using the patient query circuit 232. In an example, the query may involve searching the patient database for a matching patient who has substantially the same demographic information, medical history, or treatment history as the target patient. In another example, the query may involve searching the patient database for a matching patient whose ATH-COI is established using substantially the same physiological signals or signal metrics as those received for the target patient. In an example, the query objects, such as the patient medical record, the physiological signal or signal metrics, or contextual information, may be specified, selected, or adjusted by a user such as a clinician.

At 440, formation about ATH-COI correspondence associated with the matching patient may be retrieve from the patient database and output to a user or a process. At 450, the retrieved ATH-COI may be output to a user (e.g., a clinician) such as displayed on a display of the user interface 250. Additionally or alternatively, at 460 the retrieved ATH-COI correspondence may be used to detect future WHF event. At 462, the user may identify a desired COI from the retrieved information about the ATH-COI correspondence, such as a time to symptom (TSA) sufficient long to ensure enough time to arrange clinic visit or to provide preventive therapies prior to patient presentation of WHF symptom or sign. Detection threshold, such as onset set threshold TO, corresponding to the desired COI may be determined according to the retrieved ATH-COI correspondence.

At 464, WHF may be detected using the determined detection threshold corresponding to the desired CO, such as via the medical event detector circuit 240. A signal metric may be generated using the physiological signal. The signal metric may be trended overtime, and compared to the determined detection threshold to determine an onset or a termination of a WHF event. In some examples, a composite signal index using a combination of signal metrics derived from the one or more physiological signals may be generated. A trend of the composite signal metric may be compared to the detection threshold to detect WHF event and generate a WHF alert. A HF therapy may optionally be delivered at 466.

Figure 5:
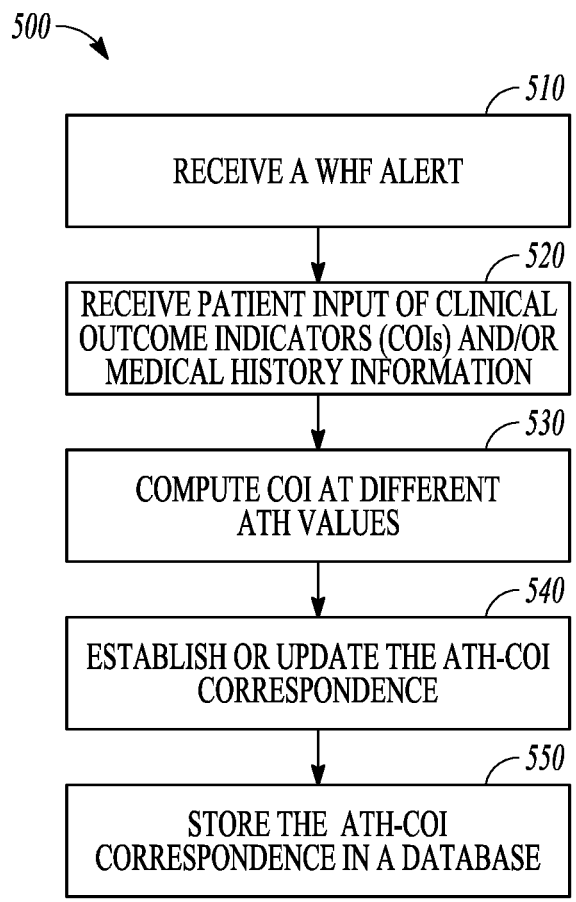
FIG. 5 illustrates generally an example of a method for establishing and maintaining a patient database of correspondence between ATHs and COIs for one or more patients.

FIG. 5 illustrates generally an example of a method 500 for establishing and maintaining a patient database of correspondence between ATHs and COIs for one or more patients. The method 500 may be implemented in and executed by the system 300 as illustrated in FIG. 3. The patient database may be updated periodically or in response to a trigger event or user command. In an example, the database is updated when a new patient is analyzed, and the ATH-COI correspondence for the new patient may be integrated into the database.

At 510, a worsening heart failure (WHF) alert may be received. The WHF alert may be generated in response to a detection of a WHF event, such as via the medical event detector circuit 240. The WHF may be detected using a signal metric generated from a physiological signal, or a composition signal metric generated from two or more physiological signals. The signal metric, or the composite signal metric, may be trended over time. The resulted signal metric trend may be compared to a preselected onset threshold to detect the target medical event. The WHF detection and the WHF alert may then trigger a process including one or more of steps 520-550 to construct a database of ATH-COI correspondence, or to update an existing database of ATH-COI correspondence, such as the patient database 222.

At 520, user input of COIs and/or medical history information may be received, such as via the COI receiver circuit 310. As previously discussed with reference to FIG. 3, the COIs may include measurements or indicators of patient response to the detection of WHF, or detector performance and its clinical implications when the detector is tuned to detect WHF using different detection thresholds. Examples of the COIs may include one or more of a time to symptom (TSA) 311, WHF information 312, a detection performance indicator 313, an intervention effectiveness indicator 314, a time to intervention 315, and a time to alert resolution 316. The COIs may be received via the user interface 250, or a mobile device configured to execute software applications to motivate the user (e.g., a patient) to enter the COI and construct or update the patient database.

In addition to the COIs, patient medical history information may be received at 520. The patient medical history information may include one or more of patient demographic information, medical history, or treatment history. The patient medical history information may additionally or alternatively include the types of physiological signals or signal metrics information (such as impedance trend, S3 heart sound trend, or a composite signal metrics trend generated using heart rate, impedance, and S3 trend), or patient contextual information such as time of day, circumstance or daily life contexts, patient environment, economic situation, medical care facilities, or caretaker responsibilities. The patient medical history information may be used to index the patients included in the patient database, such that the patient database may be searchable using one or more patient identifiers as query objects. For example, the patient database may queried according to one or more entries of patient medical history information at 430 of method 400, and identify the matching patients.

At 530, ATH may be set to different values and the COIs are evaluated at each ATH value, such as by using the database management circuit 320. In an example, the ATH may be adjusted according to a testing protocol, such as automatically incrementing or decrementing the threshold value between specified lower and upper bounds at specified step size. The outcome evaluation circuit 324 may measure one or more COIs such as any of the COIs 311-316 at different thresholds. The ATHs and the corresponding COIs may be recorded into the database at 540. The ATH-COI correspondence may be implemented as a table, an associative array, or other types of data structure and stored in the patient database at 550. The ATH-COI correspondence may be established or updated for each of a plurality of patients included in the patient database. The ATH-COI correspondence of two or more patients who have similar medical record information (e.g., demographics) or other specified patient characteristics may be merged into an aggregated ATH-COI correspondence to improve memory usage and the efficiency of patient query.

Figure 6:
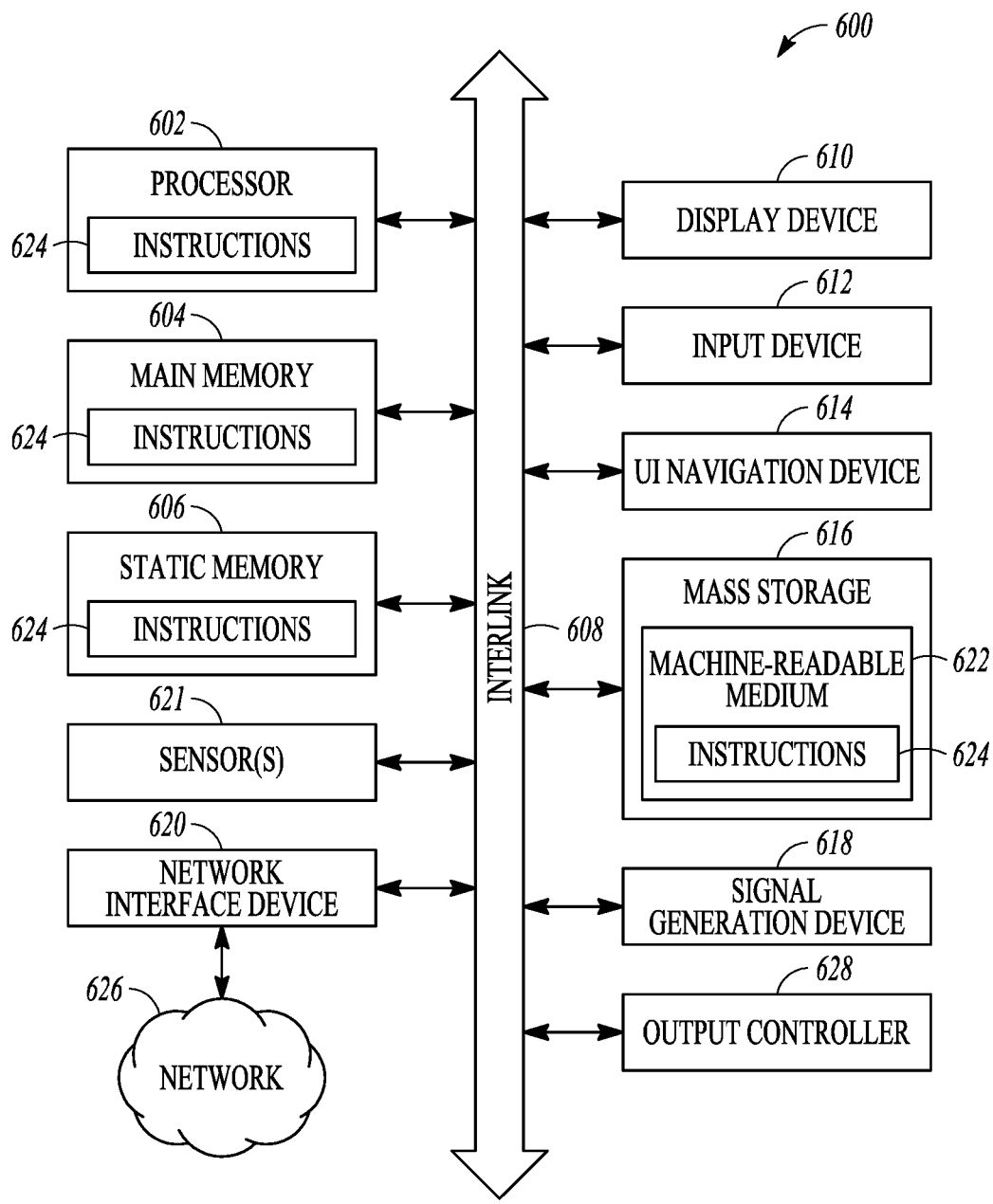
FIG. 6 illustrates generally a block diagram of an example machine upon which any one or more of the techniques (e.g., methodologies) discussed herein may perform.

FIG. 6 illustrates generally a block diagram of an example machine 600 upon which any one or more of the techniques (e.g., methodologies) discussed herein may perform. Portions of this description may apply to the computing framework of various portions of the LCP device, the IMD, or the external programmer.

In alternative embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in peer-to-peer (P2P) (or other distributed) network environment. The machine 600 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a display unit 610 (e.g., a raster display, vector display, holographic display, etc.), an alphanumeric input device 612 (e.g., a keyboard), and a user interface (UI) navigation device 614 (e.g., a mouse). In an example, the display unit 610, input device 612 and UI navigation device 614 may be a touch screen display. The machine 600 may additionally include a storage device (e.g., drive unit) 616, a signal generation device 618 (e.g., a speaker), a network interface device 620, and one or more sensors 621, such as a global positioning system (GPS) sensor, compass, accelerometer, or other sensor. The machine 600 may include an output controller 628, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 616 may include a machine readable medium 622 on which is stored one or more sets of data structures or instructions 624 (e.g., software) embodying or utilized by any one or more of the techniques or functions described herein. The instructions 624 may also reside, completely or at least partially, within the main memory 604, within static memory 606, or within the hardware processor 602 during execution thereof by the machine 600. In an example, one or any combination of the hardware processor 602, the main memory 604, the static memory 606, or the storage device 616 may constitute machine readable media.

While the machine-readable medium 622 is illustrated as a single medium, the term "machine readable medium" may include a single medium or multiple media (e.g., a centralized or distributed database, and/or associated caches and servers) configured to store the one or more instructions 624.

The term "machine readable medium" may include any medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EPSOM)) and flash memory devices; magnetic disks, such as internal hard disks and removable disks; magneto-optical disks; and CD-ROM and DVD-ROM disks.

The instructions 624 may further be transmitted or received over a communication network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 620 may include one or more physical jacks (e.g., Ethernet, coaxial, or phone jacks) or one or more antennas to connect to the communication network 626. In an example, the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 600, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should therefore be determined with references to the appended claims, along with the full scope of equivalents to which such claims are entitled.

What is claimed is:

1. A system, comprising:
    a medical event detector configured to detect a medical event from a target patient;
    a memory circuit configured to store a patient database including, for each of a plurality of patients, a correspondence between a plurality of alert thresholds (ATHs) and corresponding clinical outcome indicators (COIs); and
    a control circuit configured to establish or modify the patient database including, for one or more of the plurality of patients, adjust an ATH and evaluate a corresponding COI; and
    wherein the control circuit is configured to query the patient database for a matching patient that meets a query criteria for the target patient, and to retrieve from the patient database an ATH-COI correspondence associated with the matching patient; and
    wherein the medical event detector circuit is configured to detect the medical event from the target patient using (1) one or more physiological signals sensed from the target patient and (2) the retrieved ATH-COI correspondence associated with the matching patient, and to generate an alert of the detected medical event.

2. The system of claim 1, wherein:
    the control circuit is configured to determine an alert threshold using a user input of a COI and the retrieved ATH-COI correspondence; and
    the medical event detector circuit is configured to generate the alert of the detected medial event when a measurement of the one or more physiological signals exceeds the determined alert threshold.

3. The system of claim 2, wherein the determined alert threshold includes a composite signal index threshold, and the medical event detector circuit is configured to:
    generate a composite signal index using a combination of signal metrics derived from the one or more physiological signals; and
    generate the alert in response to the generated composite signal index exceeding the composite signal index threshold.

4. The system of claim 1, wherein the control circuit is configured to receive information about a symptom or sign of the medical event via an external device communicatively coupled to the control circuit, and to determine the plurality of COIs further using the information about the symptom or sign.

5. The system of claim 1, wherein the COI includes a time to symptom representing a time interval from an onset of the generated alert to a clinical presentation of a symptom or sign of the medical event.

6. The system of claim 1, wherein the COI includes information about a degree of severity of the medical event detected using a corresponding ATH.

7. The system of claim 1, wherein the COI includes a detection performance indicator representing statistical accuracy of a detection of the medical event using a corresponding ATH.

8. The system of claim 1, wherein the COI includes an intervention effectiveness indicator representing an efficacy of a therapy delivered in response to a detection of the medical event using a corresponding ATH.

9. The system of claim 1, wherein the COI includes a time to intervention representing a time delay from an onset of the generated alert to delivery of a therapy for treating the medical event.

10. The system of claim 1, wherein the COI includes a time to alert resolution representing a time delay from an onset of the generated alert to a reset of the generated alert.

11. The system of claim 1, comprising a therapy circuit configured to generate or adjust a therapy in response to the detection of the medical event.

12. The system of claim 1, wherein the medical event includes a worsening heart failure (WHF), and the COI includes one or more of:
a stable heart failure;
a subclinical heart failure requiring no medication change;
a non-emergent WHF requiring oral medication change;
a non-emergent WHF requiring intravenous therapy; or
an emergent WHF.

13. The system of claim 1, wherein the query criteria includes one or more of: demographic information; medical history; or treatment history.

14. The system of claim 1, wherein the control circuit is configured to query the patient database for a matching patient that meets the query criteria for the target patient based on the one or more physiological signals sensed from the target patient and physiological signal or signal metric used for establishing the ATH-COI correspondence.

15. A method, comprising:
adjusting an alert threshold (ATH) and evaluating a clinical outcome indicator (COI) corresponding to the adjusted ATH in one or more of a plurality of patients;
establishing or modifying a patient database that includes, for each of the plurality of patients, a correspondence between a plurality of alert thresholds and corresponding clinical outcome indicators;
querying the patient database for a matching patient that meets a query criteria for a target patient;
retrieving from the patient database an ATH-COI correspondence associated with the matching patient; and
detecting a medical event from the target patient, via a medical event detector circuit, using (1) one or more physiological signals sensed from the target patient and (2) an alert threshold according to the retrieved ATH-COI correspondence associated with the matching patient.

16. The method of claim 15, comprising:
determining an alert threshold using a user input of a COI and the retrieved ATH-COI correspondence; and
generate an alert of the detected medical event when a measurement of the one or more physiological signals exceeds the determined alert threshold.

17. The method of claim 16, wherein the determined alert threshold includes a composite signal index threshold, and the detecting of the medical event includes:

generating a composite signal index using a combination of signal metrics derived from the one or more physiological signals; and
generating the alert in response to the generated composite signal index exceeding the composite signal index threshold.

18. The method of claim 15, comprising:
receiving information about a symptom or sign of the medical event via an external device; and
determining the plurality of COIs using the information about the symptom or sign.

19. The method of claim 15, wherein the COI includes one or more of:
a time to symptom;
a degree of severity of the medical event;
a detection performance indicator;
an intervention effectiveness indicator;
a time to intervention; or
a time to alert resolution.

20. A system, comprising:
a medical event detector configured to detect worsening heart failure (WHF) from a target patient;
a control circuit configured to establish or modify a patient database including, for each of a plurality of patients:
adjust an ATH and evaluate a corresponding time to symptom (ToS) measurement, the ToS measurement representing a time interval from an onset of an alert to a clinical presentation of WHF; and
generate a correspondence between a plurality of alert thresholds and corresponding TOS measurements;
a memory circuit configured to store the patient database;
wherein the control circuit is configured to query the patient database for a matching patient that meets a query criteria for the target patient, and to retrieve from the patient database an ATH-ToS correspondence associated with the matching patient; and
wherein the medical event detector circuit is configured to detect WHF from the target patient using (1) one or more physiological signals sensed from the target patient and (2) the retrieved ATH-ToS correspondence associated with the matching patient, and to generate an alert of the detected WHF.

* * * * *